(12) United States Patent
Muser

(10) Patent No.: US 7,540,844 B2
(45) Date of Patent: Jun. 2, 2009

(54) CELL SCRAPER

(75) Inventor: Andrew P. Muser, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 959 days.

(21) Appl. No.: 10/912,915

(22) Filed: Aug. 6, 2004

(65) Prior Publication Data
US 2005/0065539 A1    Mar. 24, 2005

Related U.S. Application Data

(60) Provisional application No. 60/496,464, filed on Aug. 20, 2003.

(51) Int. Cl.
*A61B 1/00* (2006.01)
(52) U.S. Cl. .................... 600/570; 606/161
(58) Field of Classification Search ............ 600/570, 600/571; 606/161
See application file for complete search history.

(56) References Cited

U.S. PATENT DOCUMENTS

| | | |
|---|---|---|
| 4,892,831 A | 1/1990 | Wong |
| 5,341,538 A | 8/1994 | Banome |
| D350,603 S | 9/1994 | Firlik |
| 5,380,492 A | 1/1995 | Seymour |
| 5,477,863 A | 12/1995 | Grant |
| 5,737,803 A | 4/1998 | Tisdale |
| 5,740,586 A | 4/1998 | Gomas |
| 5,781,958 A | 7/1998 | Meessmann et al. |
| 5,900,374 A | 5/1999 | Otto-Nagels |
| 5,920,943 A | 7/1999 | Barker |
| 5,964,009 A | 10/1999 | Hoepfl et al. |
| 5,991,960 A | 11/1999 | Johnson |
| 6,194,199 B1 * | 2/2001 | Asa ................. 435/309.1 |
| 6,213,055 B1 | 4/2001 | Willinger et al. |
| 6,283,611 B1 * | 9/2001 | Sharrah et al. ......... 362/205 |
| 6,292,973 B1 | 9/2001 | Moskovich et al. |
| 6,298,516 B1 | 10/2001 | Beals et al. |
| 6,349,445 B1 | 2/2002 | Mackay et al. |
| 6,353,958 B2 | 3/2002 | Weihrauch |
| 6,383,804 B1 | 5/2002 | Ward, Jr. et al. |
| 6,464,920 B1 | 10/2002 | Kramer |
| 2002/0158423 A1 * | 10/2002 | Barinaga et al. ........ 277/630 |

FOREIGN PATENT DOCUMENTS

WO    WO 99/25251    *    2/1999

* cited by examiner

*Primary Examiner*—Walter D Griffin
*Assistant Examiner*—Shanta G Doe
(74) *Attorney, Agent, or Firm*—Hoffmann & Baron, LLP

(57) ABSTRACT

A cell scraper includes a grip, an elongate arm and a scraper blade. The cell scraper includes a substrate molded from a substantially rigid plastic. The substrate includes a blade support remote from the grip. The cell scraper also includes a resilient material over-molded onto the substrate. The resilient material may be molded onto the grip to facilitate gripping. Additionally, the resilient material is molded around the blade support to define a flexible blade for efficiently scraping cells from a tissue culture vessel.

21 Claims, 4 Drawing Sheets

CELL SCRAPER

This application claims priority of U.S. Provisional Patent Application No. 60/496,464, filed Aug. 20, 2003, which is hereby incorporated by reference.

BACKGROUND OF THE INVENTION

1. Field of the Invention

The invention relates to a cell scraper for scraping samples of tissue that accumulate in a tissue culture vessel.

2. Description of the Related Art

Many laboratory procedures require the cultivation of tissues for subsequent analysis and diagnostic tests. The tissues are cultivated in tissue culture vessels, such as flasks or petri dishes. A typical tissue culture flask is a low profile rectangular vessel with a top wall, a bottom wall and a plurality of interconnected side walls. One side wall may include an opening and a tubular neck may project angularly up from the opening to provide access to the interior of the tissue culture vessel. A cap may be mounted removably on the tubular neck for sealing the tissue culture vessel. Other tissue culture dishes include a bottom wall, a side wall enclosure and an open top. A cover may then be mounted removably to the open top of the side walls for selectively enclosing the interior of the tissue culture vessel.

Tissue culture vessels are employed by depositing a controlled amount of a liquid growth medium in the vessel. A small sample of the tissue that is to be cultivated then is deposited into the vessel. The vessel is closed by placing the cap over the tubular neck or by placing the top wall across the open top defined by the side walls. The vessel then is stored in an environment that is conducive to tissue growth. Tissue growing in the vessel must be removed and analyzed periodically. The growing tissue is likely to attach itself to the bottom wall of the vessel, and hence must be scraped from the bottom wall for analysis.

Cell scrapers are employed for removing tissue from the bottom surface of a tissue culture vessel. The typical cell scraper includes a long thin handle unitarily molded from a rigid plastic material. The handle typically tapers from a relatively large proximal end to a relatively small distal end. For example, the proximal end of the handle is likely to be approximately 0.25 inch in diameter, while the distal end is likely to be about 0.125 inch in diameter. The proximal end of the handle may be knurled to facilitate gripping by a laboratory technician. The distal end of the handle is molded to include two hinge pins.

The known cell scraper also includes a scraper blade molded unitarily from plastic, and may the same plastic as the handle. The blade includes a planar scraping edge and a pair of opposed mounting apertures that can be snapped into engagement with the hinge pins of the handle. The dimensions of the blade will vary depending upon the intended application, and specifically in accordance with the size of the tissue culture vessel. For example, a small blade is likely to be only slightly in excess of 0.5 inch wide, while a large blade is likely to be slightly in excess of one inch.

The hinge pins for mounting the blade to the handle typically are very small. For example, a hinge pin typically has a diameter in the range of 0.06-0.1 inch, and a length of comparable dimensions. As a result, the mechanical connection between the blade and the handle of the typical cell scraper is weak. The very small dimensions create the potential for improper mounting of the blade on the handle. Hence, the mounting of the blade to the handle is time consuming and costly and must be subject to considerable quality control checking.

The cell scraper typically is shipped to the laboratory in a sterile package formed by opposed layers secured in face-to-face relationship around the cell scraper. The package is opened immediately prior to use by peeling the layers away from one another and removing the cell scraper from the opened package. The laboratory technician opens the tissue culture vessel. The technician then holds the knurled proximal end of the handle in one hand while inserting the blade at the distal end of the scraper into the tissue culture vessel. The blade pivots about the hinge pins to align with the bottom surface of the vessel in response to forces exerted on the handle by the technician. The technician then slides the blade across the bottom surface of the tissue culture vessel, while maintain a perpendicular force to the growth surface, so that a sample of the cultured cells can be scraped from the bottom. The cells are then washed from the tissue culture vessel for analysis. Perpendicular and lateral forces exerted on the blade easily can dislodge the blade from the handle of the cell scraper. These forces can be exerted during the initial insertion of the blade into the tissue culture vessel, during the removal of the blade from the tissue culture vessel or during the cell scraping process. The separated blade cannot be retrieved easily without adversely affecting the tissue culturing process. Hence, the laboratory must then incur the expense for an additional cell scraper and creates the risk of contaminating the tissue culture vessel.

Occasionally it may be necessary to access difficult to reach areas of a tissue culture vessel, such as corners of the vessel or areas near the opening to a flask of the vessel. The pivoting of the blade on the handle may facilitate access to remote areas of the tissue culture vessel. However, the rigid plastic blade is not ideal for removing cell cultures from surfaces that are difficult to reach. A more resilient blade could be more effective for removing cell cultures from surfaces that are not perfectly planar. However, a more resilient blade would not be as effective for gripping the hinge pins of the scraper handle and would separate from the hinge pins more easily.

The knurling that is molded into the handle of the cell scraper contributes somewhat to the digital manipulation of the scraper. However, knurling can have only a minimal effect on the ability to manipulate the scraper in view of the relatively small cross-section of the handle.

Some tools have been molded with handles formed from two different types of materials to facilitate gripping. A first material is a more rigid thermoplastic and provides structural support for the handle. A second material is over-molded or co-molded with the more rigid material and is more resilient. The more resilient material facilitates gripping. Such over-molding is commonly used in handles of toothbrushes and other hand-held tools. The more rigid thermoplastic material then extends from the gripping region of the toothbrush or other tool to the distal working end of the toothbrush or tool.

SUMMARY OF THE INVENTION

The invention is a cell scraper for use with tissue culture vessels, such as tissue culture flasks, petri dishes and the like. The cell scraper includes an elongate handle having a proximal end to be gripped by a laboratory technician and a distal end for scraping cells. The cell scraper is formed integrally from two different types of material. A first material is a substantially rigid thermoplastic material, such as polypropylene, and is selected to provide structural support for the cell scraper. The more rigid materials extends from the proximal end of the cell scraper to a location near the distal end. Portions of the more rigid material near the proximal end preferably are molded into a shape that is conducive to manual gripping. Additionally, the more rigid material may be molded with recesses near the proximal end of the cell scraper. Portions of the more rigid material near the distal end preferably define a blade support. The blade support may be sufficiently thin to permit a controlled flexion of the blade support. Alternatively, a living hinge may be formed on or near the blade support to provide flexion of the blade support around at least one selected axis.

The cell scraper further includes a more resilient material, such as a thermoplastic elastomer with a lower durometer than the rigid material incorporated into the cell scraper. The resilient material is co-molded or molded over portions of the more rigid material, including the blade support, and defines at least a blade at the distal end of the cell scraper. Additionally, the resilient material may be molded into recesses formed in the more rigid material near the proximal end of the cell scraper. The resilient material of the blade is able to flex and conform to surface irregularities of the tissue culture vessel. However, the resilient material of the blade will return to or towards an undeformed molded shape for the blade. Thus, the resilient material of the blade is well suited to scraping cell cultures from both easy and difficult to reach areas of the tissue culture vessel, while the resilient material that may be molded into recesses at the proximal end of the cell scraper facilitates gripping and manipulation.

The integral engagement of the more resilient material of the blade with the more rigid supporting material of the handle prevents separation of the blade from the handle as had occurred frequently with known cell scrapers. Additionally, the resilient characteristics of the blade still permits the maximum blade area to be in contact with the growth surface of the cells, and hence ensure more effective scraping of cell cultures.

BRIEF DESCRIPTIONS OF THE DRAWINGS

DETAILED DESCRIPTION

Figure 1:
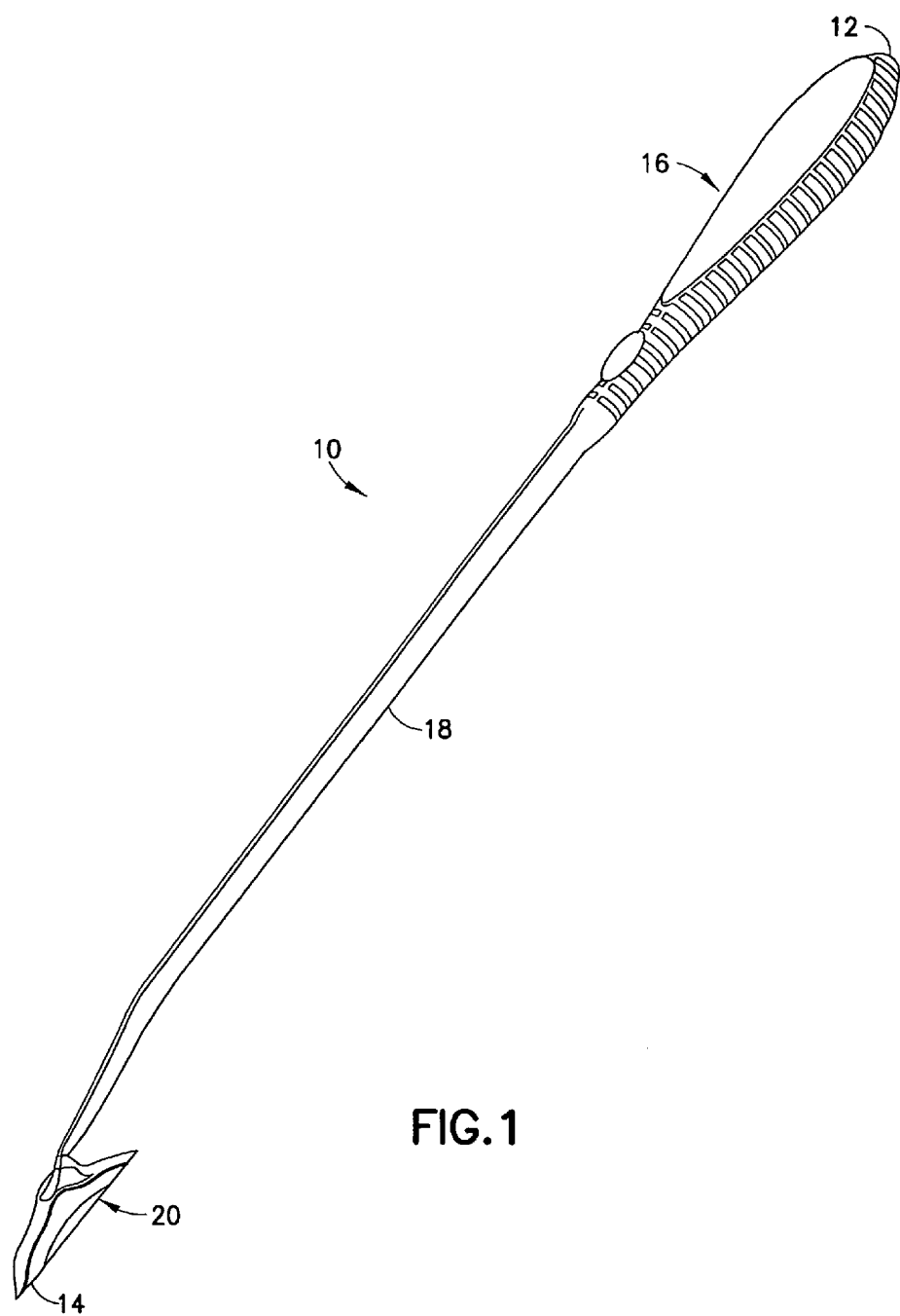
FIG. 1 is a perspective view of a cell scraper in accordance with the subject invention.
Figure 2:
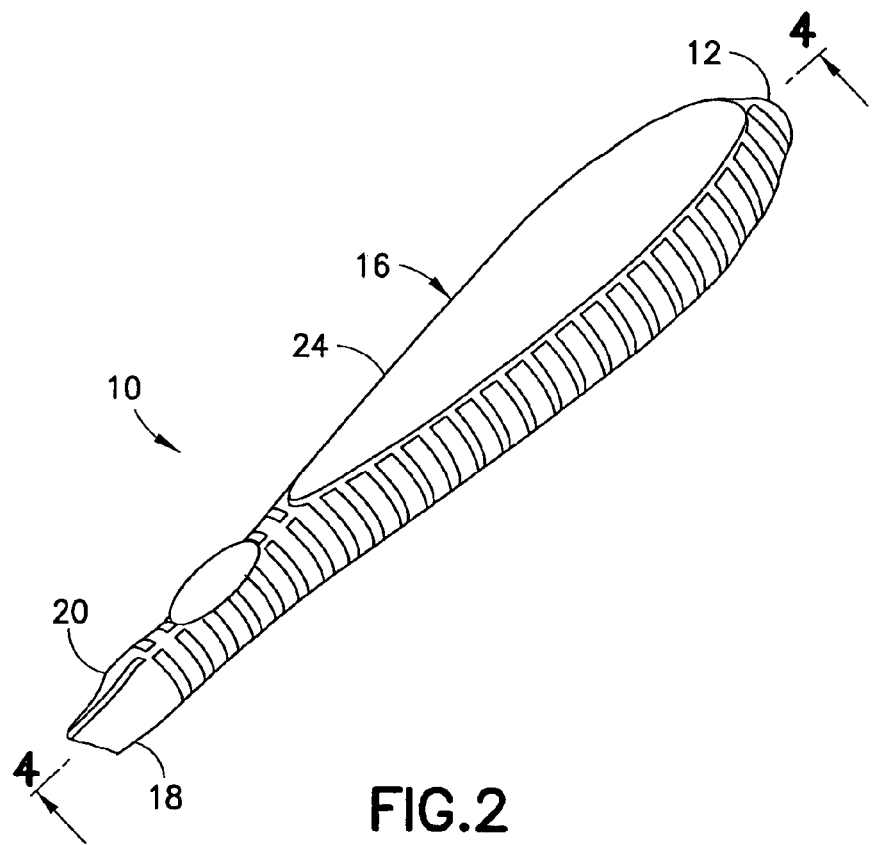
FIG. 2 is an enlarged perspective view of the proximal end of the cell scraper.
Figure 3:
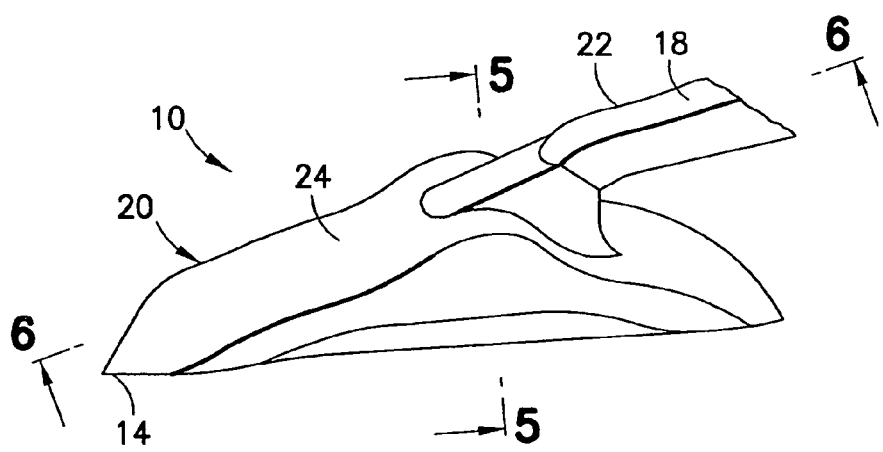
FIG. 3 is an enlarged perspective view of the distal end of the cell scraper.

A cell scraper in accordance with the invention is identified generally by the numeral 10 in FIGS. 1-6. Cell scraper 10 includes a proximal end 12 and a distal end 14. A grip 16 is defined adjacent proximal end 12 of cell scraper 10. An elongate arm 18 extends distally from grip 16 and a blade 20 is defined adjacent distal end 14.

Cell scraper 10 is formed by an over-molding process and includes a substrate 22 formed from polypropylene or other substantially rigid thermoplastic material. Substrate 22 extends from proximal end 12 to a location near distal end 14. Scraper 10 further includes a low durometer thermoplastic elastomer 24 that is over-molded onto substrate 22 at selected regions along the length of cell scraper 10. In particular, thermoplastic elastomer 24 is over-molded on distal portions of substrate 22 to define major portions of blade 20. Additionally, thermoplastic elastomer 24 is over-molded onto portions of substrate 22 along grip 16.

Figure 4:
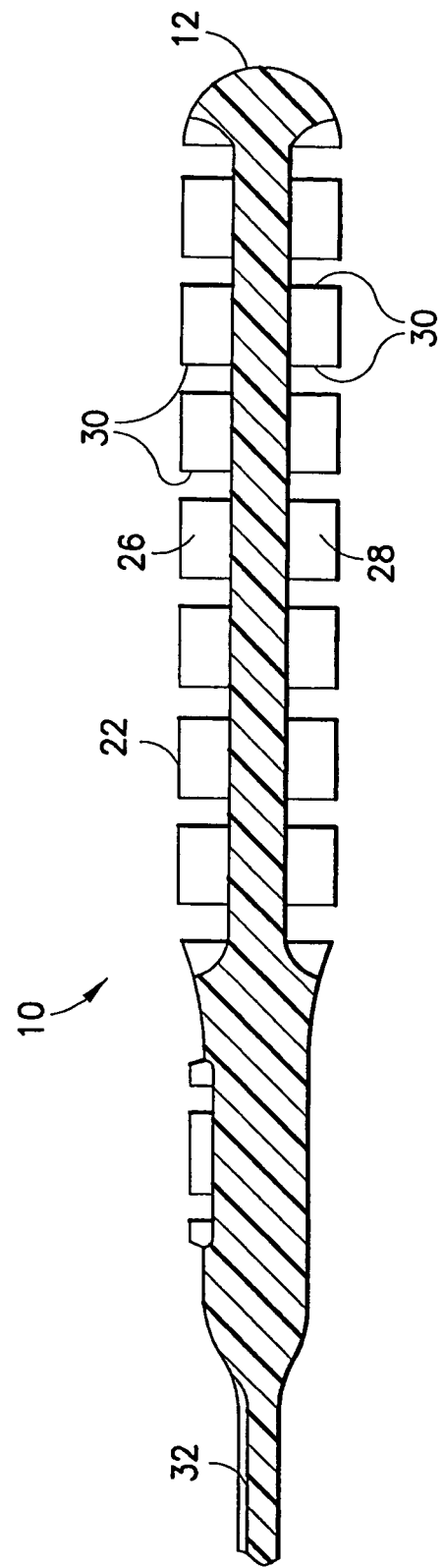
FIG. 4 is a cross-sectional view taken along line 4-4 in FIG. 2, but without the elastomer.
Figure 5:
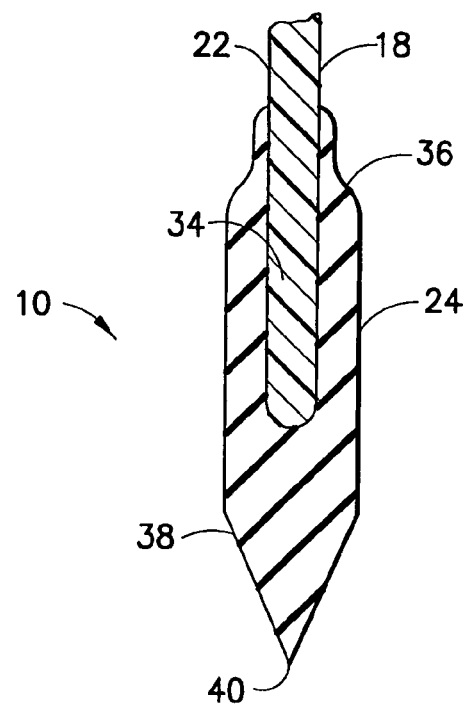
FIG. 5 is a cross-sectional view taken along line 5-5 in FIG. 3.
Figure 6:
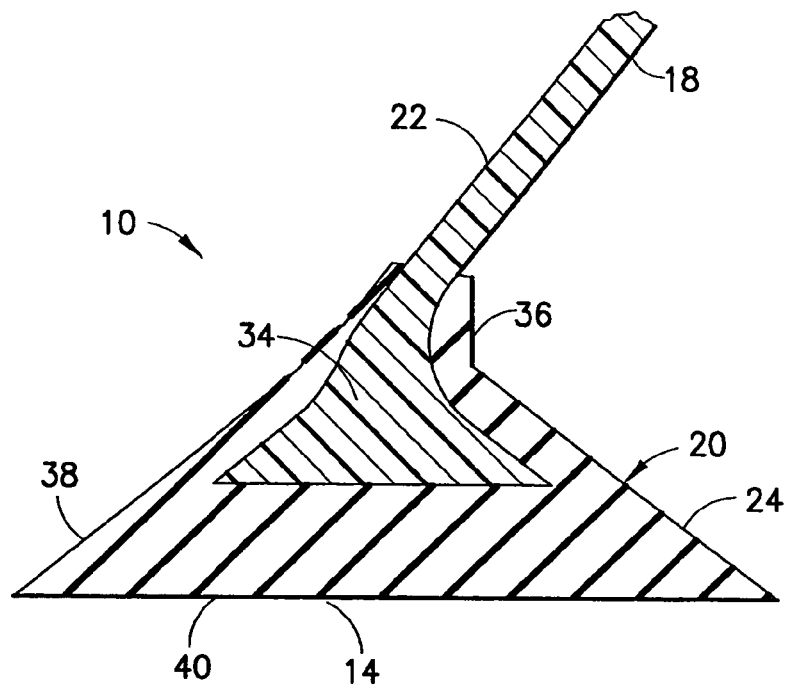
FIG. 6 is a cross-sectional view taken along line 6-6 in FIG. 3.

As shown in FIG. 4, portions of substrate 22 at grip 16 define top and bottom recesses 26 and 28 and a plurality of openings 30 throughout the grip 16 to provide communication between recesses 26 and 28. Portions of substrate 22 distally of grip 16 include a narrow groove 32 extending along one longitudinal side of elongate arm 18. Groove 32 is provided to contribute to a controlled flexibility of elongate arm 18, to provide an aesthetic accent and to provide a visual cue for rotational orientation as explained herein. Portions of substrate 22 near distal end 14 are widened from arm 18 and define a generally planar blade support 34, as shown in FIGS. 5 and 6. Portions of blade support 34 in proximity to elongate arm 18 may be thinned sufficiently to permit controlled flexion of blade support 34. Flexion can be increased further around at least one axis by molding substrate 22 with a living hinge on blade support 34 or between blade support 34 and elongate arm 18.

Substrate 22 may be supported in a mold (not shown) that conforms to the overall outer shape of cell scraper 10, as shown in FIG. 1. This mold is cross-sectionally larger than substrate 22 at certain locations, including recesses 26 and 28 and grooves 30 in grip 16, groove 32 in elongate arm 18 and regions around blade support 34. A molten thermoplastic elastomer 24 then is injected into the mold cavity to fill recesses 26 and 28 and openings 30 in grip 16 and to fill longitudinal groove 32 on arm 18. The elastomer may alternatively be injected into the grip 16 and blade 20 independently. The molten thermoplastic elastomer also fills the mold cavity surrounding blade support 34 to define blade 20. Blade 20 includes a mounting section 36 that integrally surrounds all of blade support 34 and that surround distal portions of elongate arm 18 adjacent blade support 34. Thus, blade 20 is secured integrally to elongate arm 18 with no possibility of separation during use. Blade 20 further includes a flexible scraping section 38 that converges into a linear scraping edge 40 substantially at distal end 14 of cell scraper 10, as shown in FIGS. 5 and 6. Flexible scraping section 38 is spaced from blade support 34, and hence can deform so that scraping edge 40 conforms to the specific contour of the tissue culture vessel.

Cell scraper 10 is employed substantially in the conventional manner. In particular, the laboratory technician grips grip 16. However, thermoplastic elastomer 24 fills recesses 26 and 28 and grooves 30 on grip 16 and provides a more resilient surface for enhanced gripping. The laboratory technician then urges blade 20 and adjacent portions of elongate arm 18 into the tissue culture vessel. Elongate arm 18 exhibits sufficient rigidity to permit accurate positioning and guiding of blade 20 toward a targeted culture of cells in the vessel. Elastomer 24 in groove 32 of elongate arm 18 provides visual cues for directing blade 20 toward the targeted culture of cells and provides visual cues to indicate any rotational tilting of cell scraper 10 about the longitudinal axis of elongate arm 18. The technician then urges scraping edge 40 of blade 20 along the surface of the tissue culture vessel. Flexible section 38 of blade 20 is not restrained by blade support 34, and hence scraping edge 40 can conform to the specific contour of the targeted surface of the tissue culture vessel. The technician then removes blade 20 from the vessel so that the collected cells can be analyzed.

What is claimed is:

1. An elongate cell scraper having opposite proximal and distal ends, a grip being defined adjacent said proximal end, an arm extending distally from said grip and a scraper blade extending from said arm to said distal end, said cell scraper including a unitary substrate extending from said grip, along said arm and toward said distal end, a distal portion of said substrate defining a blade support, said cell scraper further comprising a resilient material integrally disposed on said substrate, said resilient material surrounding said blade support and extending unitarily from said blade support to said distal end of said cell scraper, portions of said cell scraper formed from said resilient material including a flexible blade projecting distally beyond said support, wherein said blade support is formed from a different material than said resilient material.

2. The cell scraper of claim 1, wherein said flexible blade tapers from said distal end of said cell scraper towards said substrate.

3. The cell scraper of claim 2, wherein the flexible blade comprises a linear edge at said distal end of said cell scraper.

4. The cell scraper of claim 3, wherein portions of said arm adjacent said grip are substantially linearly aligned, said edge of said flexible blade being aligned at an acute angle to portions of said arm adjacent said grip.

5. The cell scraper of claim 1, wherein the blade support is substantially planar.

6. The cell scraper of claim 5, wherein portions of said arm adjacent said blade support are substantially cylindrical, said resilient material extending proximally from said blade support and integrally surrounding and engaging portions of said arm adjacent said blade support.

7. The cell scraper of claim 6, wherein portions of said blade support in proximity to said arm are thinned sufficiently to permit flexion of said blade support in response to forces exerted thereon.

8. The cell scraper of claim 7, wherein said portion of said blade in proximity to said arm defines a living hinge.

9. The cell scraper of claim 1, wherein portions of said substrate defining said grip include a plurality of recesses, said resilient material integrally filling said recesses to define gripping regions on said grip.

10. The cell scraper of claim 1, wherein portions of said substrate defining said arm include an elongate groove extending distally from said grip, said resilient material integrally filling said groove to define visual cue regions to identify longitudinal and rotational orientation of said cell scraper.

11. The cell scraper of claim 1, wherein the resilient material is a thermoplastic elastomer.

12. The cell scraper of claim 1, wherein the substrate is formed from polypropylene.

13. A cell scraper having opposite proximal and distal ends, a grip being formed adjacent said proximal end, an elongate arm projecting distally from said grip and a scraper blade extending from said arm to said distal end, said cell scraper including a substrate unitarily molded from a thermoplastic material and extending from said grip, said substrate defining at least one recess in said grip and a blade support at an end of said arm remote from said grip, said cell scraper further including an elastomer integrally molded over at least part of said substrate, said elastomer filling said recess in said grip for defining at least one gripping region, said elastomer further covering said blade support and extending unitarily from said blade support to define a flexible blade which tapers to a substantially linear edge at said distal end, wherein said blade support is formed from a different material than said elastomer.

14. The cell scraper of claim 13, wherein said substrate is of a first color, and wherein said elastomer is of a second color.

15. The cell scraper of claim 13, wherein the substrate is molded from polypropylene.

16. The cell scraper of claim 13, wherein the elastomer is a thermoplastic elastomer.

17. A cell scraper having a handle, an arm extending unitarily from said handle and a blade support extending unitarily from said arm, a blade formed from a material having a lower durometer than the blade support, the arm and the handle, the blade being molded to define a first unitary matrix of resilient material surrounding at least portions of said blade support and extending beyond said blade support to define a flexible blade.

18. The cell scraper of claim 17, further comprising at least one recess formed in said handle, a second unitary matrix of said resilient material being disposed in said recess of said handle for facilitating gripping of said handle.

19. The cell scraper of claim 18, wherein said at least one recess in said handle comprises a plurality of interconnected recesses, said second unitary matrix of said resilient material extending into each of said recesses in said handle.

20. The cell scraper of claim 19, wherein the arm is formed with at least one longitudinal groove, said second unitary matrix of resilient material extending into said groove of said arm for providing an indication of rotational orientation of said cell scraper.

21. The cell scraper of claim 20, wherein the first and second unitary matrices of resilient material are formed from a thermoplastic elastomer having a color different from colors defined on said handle and said arm.

* * * * *